(12) United States Patent
Winsor et al.

(10) Patent No.: US 8,211,089 B2
(45) Date of Patent: Jul. 3, 2012

(54) INTRAVENOUS INJECTION SITE WITH SPLIT SEPTUM AND PRESSURE ACTIVATED FLOW CONTROL VALVE

(75) Inventors: Chris Winsor, Olathe, KS (US); Larry C. Smith, Shawnee, KS (US); W. Cary Dikeman, Lenexa, KS (US)

(73) Assignee: Nexus Medical, LLC, Lenexa, KS (US)

( * ) Notice: Subject to any disclaimer, the term of this patent is extended or adjusted under 35 U.S.C. 154(b) by 1367 days.

(21) Appl. No.: 11/277,471

(22) Filed: Mar. 24, 2006

(65) Prior Publication Data

US 2007/0225648 A1 Sep. 27, 2007

(51) Int. Cl.
*A61M 31/00* (2006.01)
(52) U.S. Cl. ........ 604/523; 604/533; 604/534; 604/535; 604/536; 604/537; 604/538; 604/539; 604/284
(58) Field of Classification Search .................. 604/523, 604/533–539
See application file for complete search history.

(56) References Cited

U.S. PATENT DOCUMENTS

| | | | |
|---|---|---|---|
| D320,082 S | 9/1991 | Wyatt et al. | |
| D323,709 S | 2/1992 | Wyatt et al. | |
| D323,889 S | 2/1992 | Wyatt et al. | |
| 5,171,234 A * | 12/1992 | Jepson et al. | 604/534 |
| 5,188,620 A * | 2/1993 | Jepson et al. | 604/534 |
| 5,199,948 A * | 4/1993 | McPhee | 604/86 |
| 5,251,873 A | 10/1993 | Atkinson et al. | |
| 5,295,657 A | 3/1994 | Atkinson | |
| 5,295,658 A | 3/1994 | Atkinson et al. | |
| 5,300,034 A * | 4/1994 | Behnke et al. | 604/167.02 |
| 5,356,396 A | 10/1994 | Wyatt et al. | |
| 5,360,413 A | 11/1994 | Leason et al. | |
| 5,402,982 A | 4/1995 | Atkinson et al. | |
| 5,501,426 A | 3/1996 | Atkinson et al. | |
| 5,533,708 A | 7/1996 | Atkinson et al. | |
| 5,578,059 A * | 11/1996 | Patzer | 604/249 |
| 5,603,706 A | 2/1997 | Wyatt et al. | |

(Continued)

OTHER PUBLICATIONS

Canadian Office Action dated Aug. 31, 2011, in Canadian Application No. 2,647,795; Filed: Sep. 24, 2008; Title: Intravenous Injection Site Split Septum and Pressure Activiated Flow Control Valve; Applicant: Winsor, Chris et al.

(Continued)

*Primary Examiner* — Nicholas Lucchesi
*Assistant Examiner* — Scott Medway
(74) *Attorney, Agent, or Firm* — Hovey Williams LLP

(57) ABSTRACT

An improved injection site (12) for infusion of parenteral fluids and the like is provided, having a pressure-actuated valve (20) and a novel split septum unit (24), which effectively prevent reflux of blood into the assembly (10). The septum unit (24) includes a resilient split septum body (64) which is precompressed so that the septum body (64) is caused to protrude proximally (78) upon insertion of a cannula (16). Consequently, upon removal of the cannula (16), there is essentially no "drumming" or creation of friction-induced negative pressures sufficient to generate blood reflux. The preloaded septum body (64) also has its proximal surface (74) essentially flush and coplanar with the adjacent proximal end (66*b*) of the tubular septum holder (66) to enhance the cleanliness of the unit (24). The specialized well (46) and septum unit (24) afford a resilient seal between the periphery of the septum body (64) and the surface (50), and a separate hard-surface seal between the outer margin of the surface (50) and the septum holder (66).

12 Claims, 4 Drawing Sheets

U.S. PATENT DOCUMENTS

| | | | |
|---|---|---|---|
| 5,632,735 A | 5/1997 | Wyatt et al. | |
| 5,685,866 A * | 11/1997 | Lopez | 604/249 |
| 5,820,601 A * | 10/1998 | Mayer | 604/167.02 |
| 5,961,497 A * | 10/1999 | Larkin | 604/246 |
| 6,022,339 A * | 2/2000 | Fowles et al. | 604/411 |
| 6,213,973 B1 * | 4/2001 | Eliasen et al. | 604/93.01 |
| 6,261,266 B1 | 7/2001 | Jepson et al. | |
| 6,607,508 B2 * | 8/2003 | Knauer | 604/131 |
| 6,669,681 B2 | 12/2003 | Jepson et al. | |
| 7,470,261 B2 * | 12/2008 | Lynn | 604/256 |
| 7,608,065 B2 * | 10/2009 | Glenn | 604/288.02 |
| 7,628,774 B2 * | 12/2009 | Fangrow, Jr. | 604/247 |
| 2004/0102738 A1 | 5/2004 | Dikeman et al. | |
| 2005/0010176 A1 | 1/2005 | Dikeman et al. | |

OTHER PUBLICATIONS

Australian Office Action dated Nov. 1, 2011, in Australian Application No. 2007230722; Filed: Mar. 22, 2007; Title: Intravenous Injection Site Split Septum and Pressure Activiated Flow Control Valve; Applicant: Winsor, Chris et al.

* cited by examiner

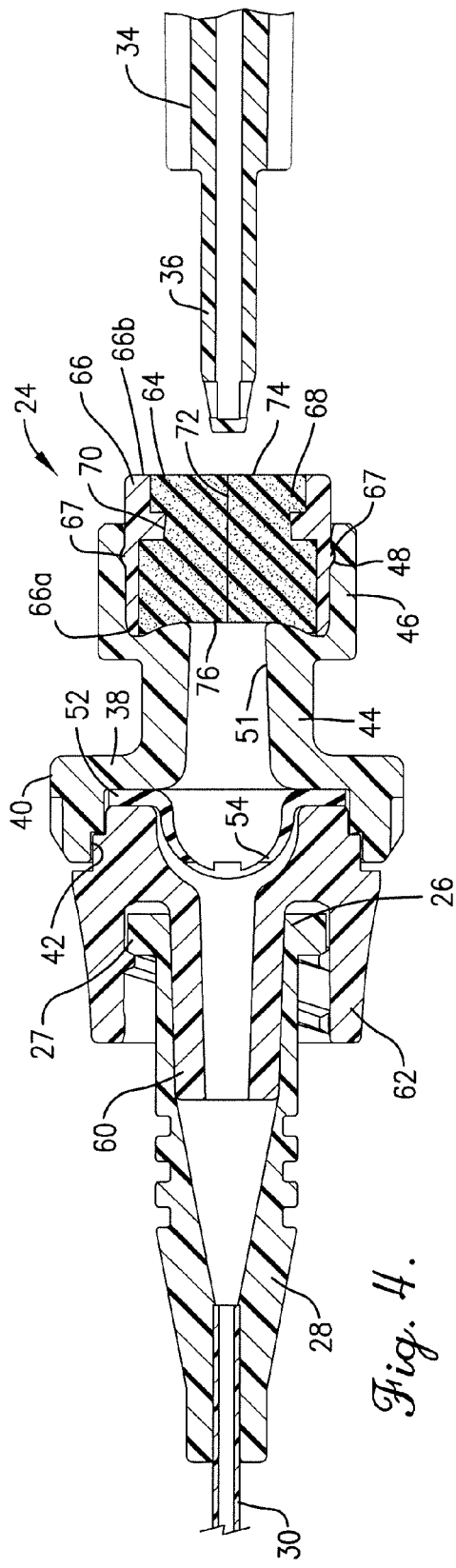
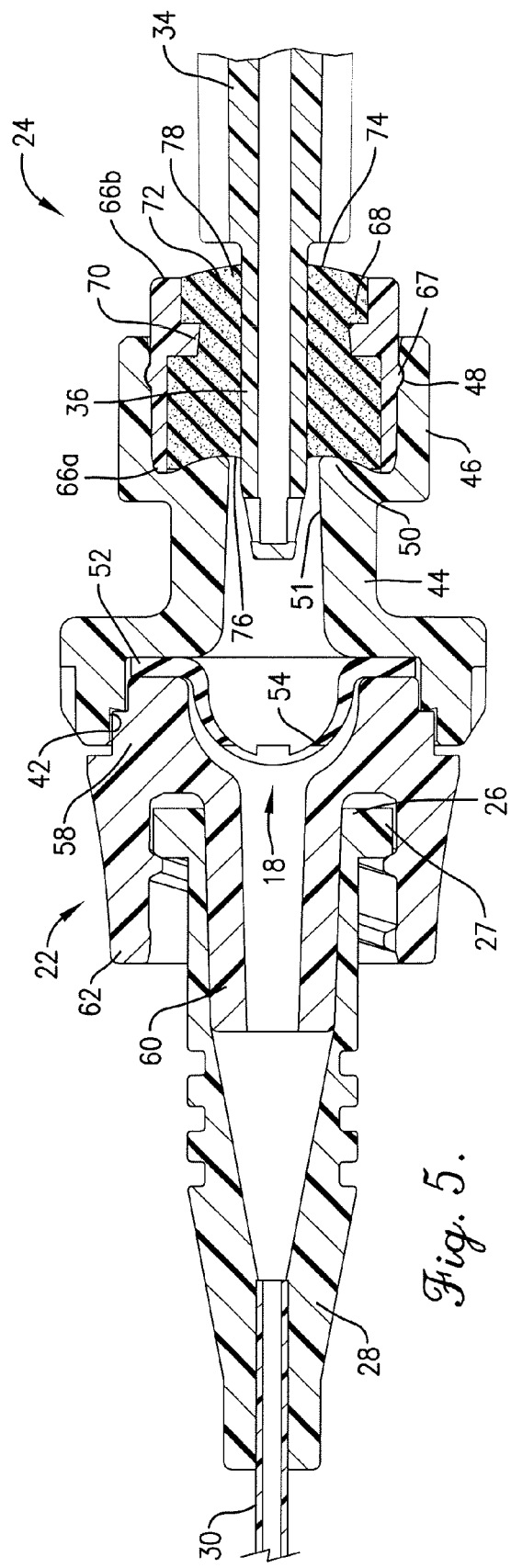
Fig. 4.
Fig. 5.

INTRAVENOUS INJECTION SITE WITH SPLIT SEPTUM AND PRESSURE ACTIVATED FLOW CONTROL VALVE

BACKGROUND OF THE INVENTION

1. Field of the Invention

The present invention is broadly concerned with infusion devices used for the administration of various fluids to patients. More particularly, the invention is concerned with such devices having a resilient and deformable split septum unit for sealingly receiving a cannula. More preferably, the device also includes a pressure-actuated flow control device downstream from the septum for reducing the risk of blood reflux into the device during use.

2. Description of the Prior Art

The use of intravenous devices for the administration of parenteral and other fluids to patients is a common practice. A variety of devices for such purposes have been proposed in the past, such as a simple length of tubing having a fitting on one end for making connection with a source of fluid (e.g., a bottle or flexible bag), while the other end is provided with a needle or catheter which may be inserted into the vein of a patient. More commonly, however, specialized infusion devices are provided which include a venous needle (or catheter) at one end and a split septum at the other end. In the use of these devices, the needle (or catheter) is inserted into the patient and the device is taped or otherwise affixed to the patient or adjacent equipment. Thereupon, a cannula connected to a liquid supply may be inserted into the free septum end of the device in order to begin fluid therapy. The septum provides a swabable injection site that can be reused, while the needle (or catheter) remains inserted into the patient. Such devices are illustrated, e.g., in U.S. Pat. Nos. 5,632,735, 5,603,706, 5,356,396,, D320,082, D323,709,, and D323,889, (hereinafter "the Wyatt patents").

A persistent problem with prior infusion devices is referred to as blood reflux, or the tendency for small amounts of blood from the patient to be drawn into the infusion apparatus. Among other things, this leads to clotting of the blood and occlusion of the apparatus and the need for frequent device replacement. This can be traumatizing to patients, and requires continual monitoring of the apparatus by the nursing staff. Furthermore, untrained patient treatment personnel can often over-pressurize the IV system in an effort to dislodge the occlusion, which can disconnect IV tubing or, more importantly, severely injure the patient. A prime cause of undesired and inadvertent blood reflux in prior devices stems from the negative pressures generated by removal of the cannula. Split septums further exacerbate the problem. Particularly, removal of the cannula causes a frictional pullback on the septum and resultant creation of negative pressures owing to consequent distal distortion of the septum (sometimes referred to as "drumming").

There is accordingly a need in the art for improved infusion devices equipped with split septum units and which eliminate the possibility of blood reflux upon cannula removal.

SUMMARY OF THE INVENTION

The present invention overcomes the problems outlined above, and provides an improved infusion assembly for safe and effective administration of fluids to patients, while essentially eliminating any possibility of blood reflux. More specifically, according to one aspect of the present invention, the present invention concerns an intravenous injection site for connection to a cannula, wherein the injection site comprises a split septum unit including a resilient septum body. The septum body presents opposite proximal and distal faces and a slit extending therebetween to receive the cannula. The injection site further comprises a pressure-actuated flow control valve spaced distally from the septum body and operable to selectively prevent fluid flow in a proximal direction. The injection site also includes a septum support assembly operable to precompress the septum body so that, upon insertion of the cannula, the resilient septum body is displaced proximally to a greater degree than the septum body is displaced distally.

According to another aspect of the present invention, the intravenous injection site includes a split septum unit including a resilient septum body, wherein the body presents opposite proximal and distal faces and a slit extending therebetween to receive a cannula. The injection site also includes a support body supporting the split septum unit and including an annular septum-engaging surface that presents a flow-through passageway. The septum-engaging surface contacts the distal face of the septum body and thereby restricts distal displacement of the septum body when the cannula is inserted therein.

In addition, one aspect of the present invention concerns a intravenous injection site including a split septum unit comprising a resilient septum body that presents opposite proximal and distal faces and a slit extending therebetween to receive the cannula. The split septum unit includes a septum holder disposed about the septum body. The injection site also includes a support body supporting the split septum unit and including a septum well receiving the septum unit therein. A first seal is defined between the bodies, and a second seal is defined between the septum holder and the support body.

Yet another aspect of the present invention concerns an intravenous injection site including a split septum unit including a resilient septum body, wherein the body presents opposite proximal and distal faces and a slit extending therebetween to receive the cannula. The site also includes a septum support assembly presenting a terminal proximal face. The proximal faces of the septum support assembly and the septum body are substantially flush to cooperatively present a substantially smooth swabable proximal surface. This eliminates undercut regions prone to contamination, thus improving the cleanliness of the septum unit The septum body is preferably precompressed so that, upon insertion of a cannula, the resilient body is displaced proximally and is prevented from substantial displacement distally. It has been discovered that such preloading of the resilient septum body prevents generation of any significant negative pressures (or "drumming") upon removal of the cannula, thus eliminating one of the prime causes of blood reflux.

In preferred forms, the pressure-actuated flow control valve is of split concavo-convex configuration. This valve is described in detail in US Published Patent Application 2005/0010176, which is incorporated by reference herein.

Other preferred features of the invention include a double seal effected between the support body and septum unit. Specifically, a first seal is afforded because of the engagement between the periphery of the resilient septum body and the protruding well surface, and a second hard-surface seal is provided between the outer margin of the well surface and the annular septum holder.

Other aspects and advantages of the present invention will be apparent from the following detailed description of the preferred embodiments and the accompanying drawing figures.

BRIEF DESCRIPTION OF THE DRAWINGS

Preferred embodiments of the invention are described in detail below with reference to the attached drawing figures, wherein:

FIG. 4 is a cross-sectional view of the FIG. 1 injection site, prior to insertion of the cannula; and FIG. 5 is a vertical sectional view similar to that of FIG. 4, but showing the device after insertion of the cannula with resultant proximal displacement of the split septum.

Figure 1:
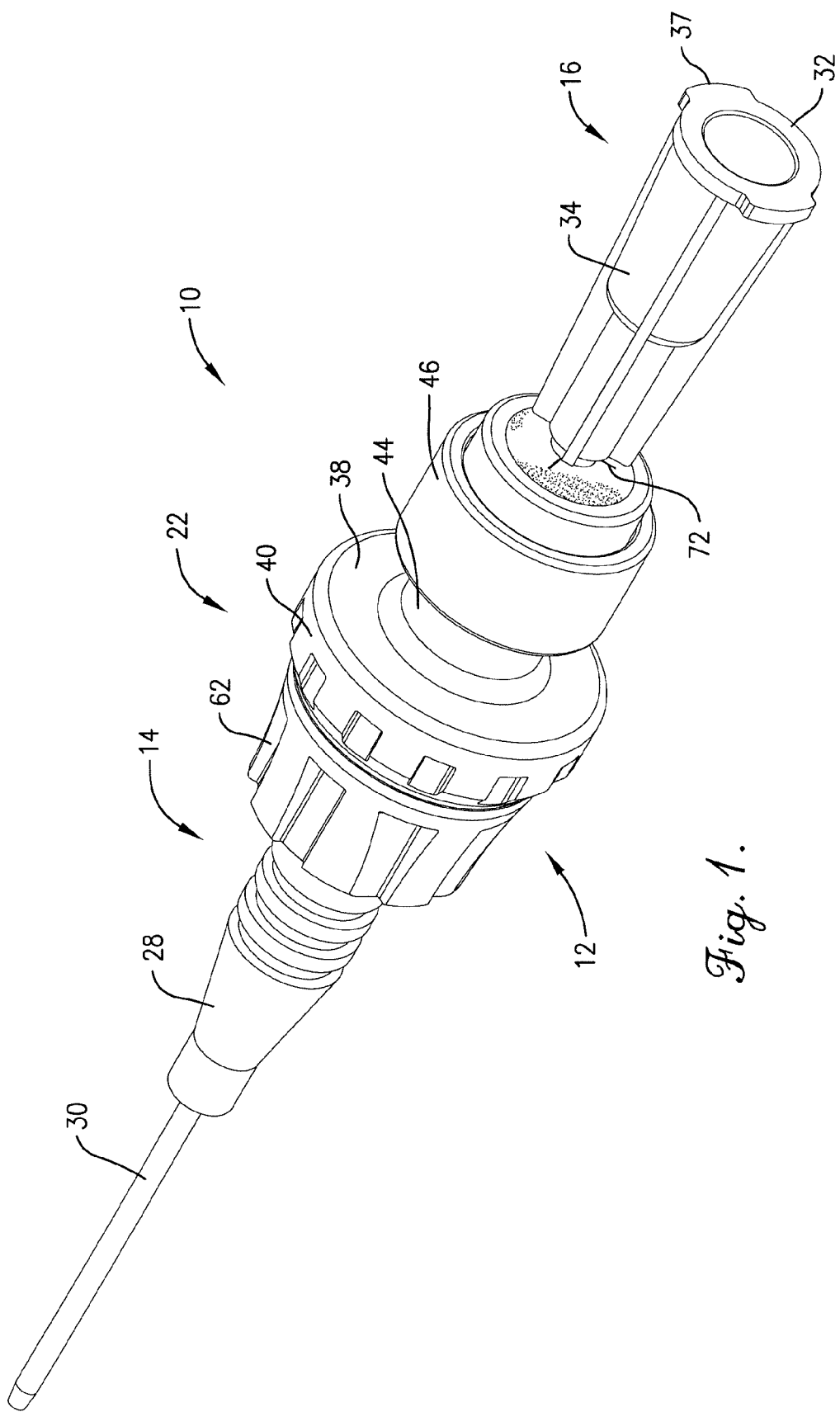
FIG. 1 is a perspective view of an intravenous injection site constructed in accordance with a preferred embodiment of the present invention, and being shown in use with a peripheral catheter and blunt cannula.
Figure 2:
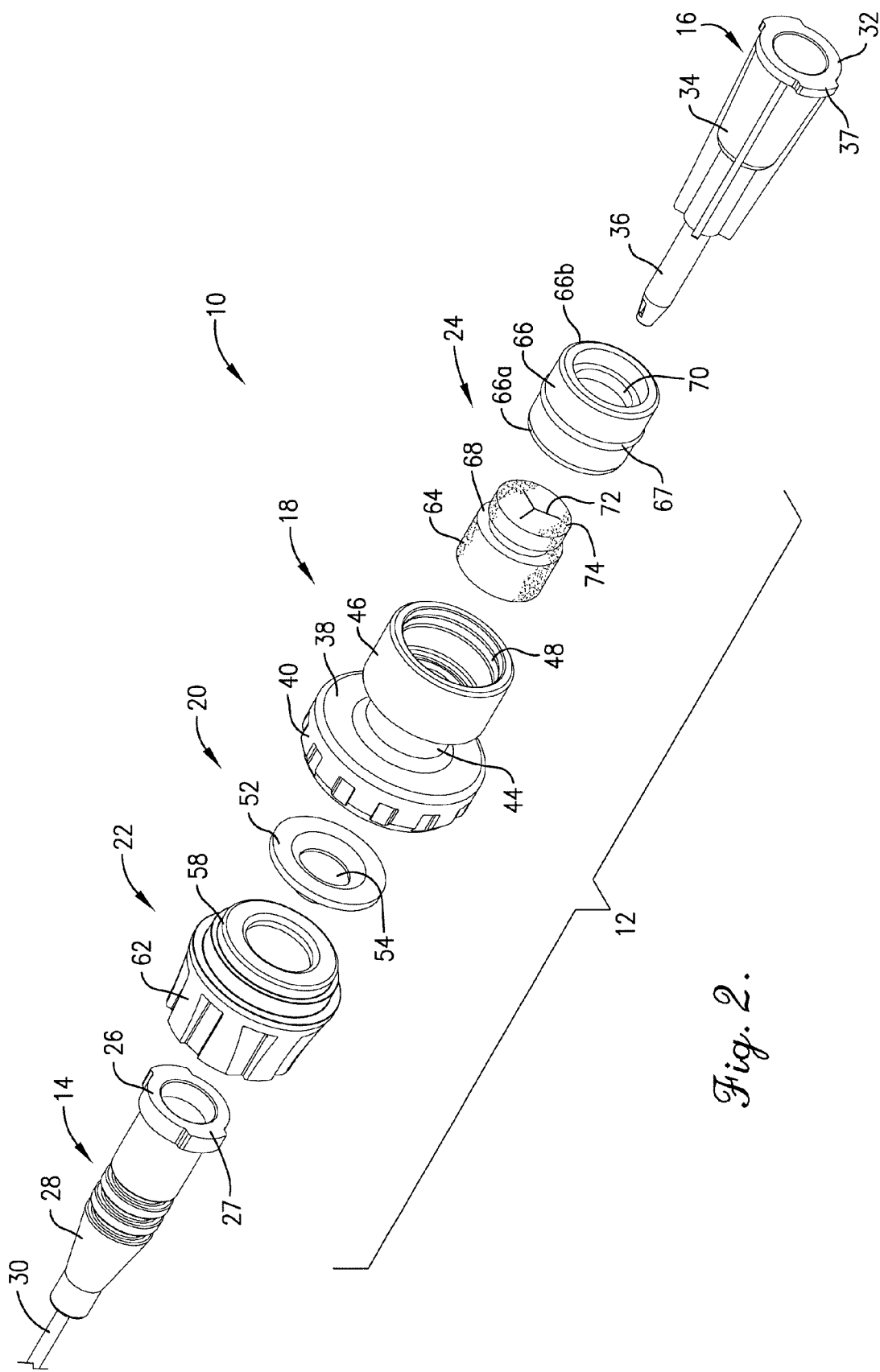
FIG. 2 is an exploded perspective view of the injection site depicted in FIG. 1.
Figure 3:
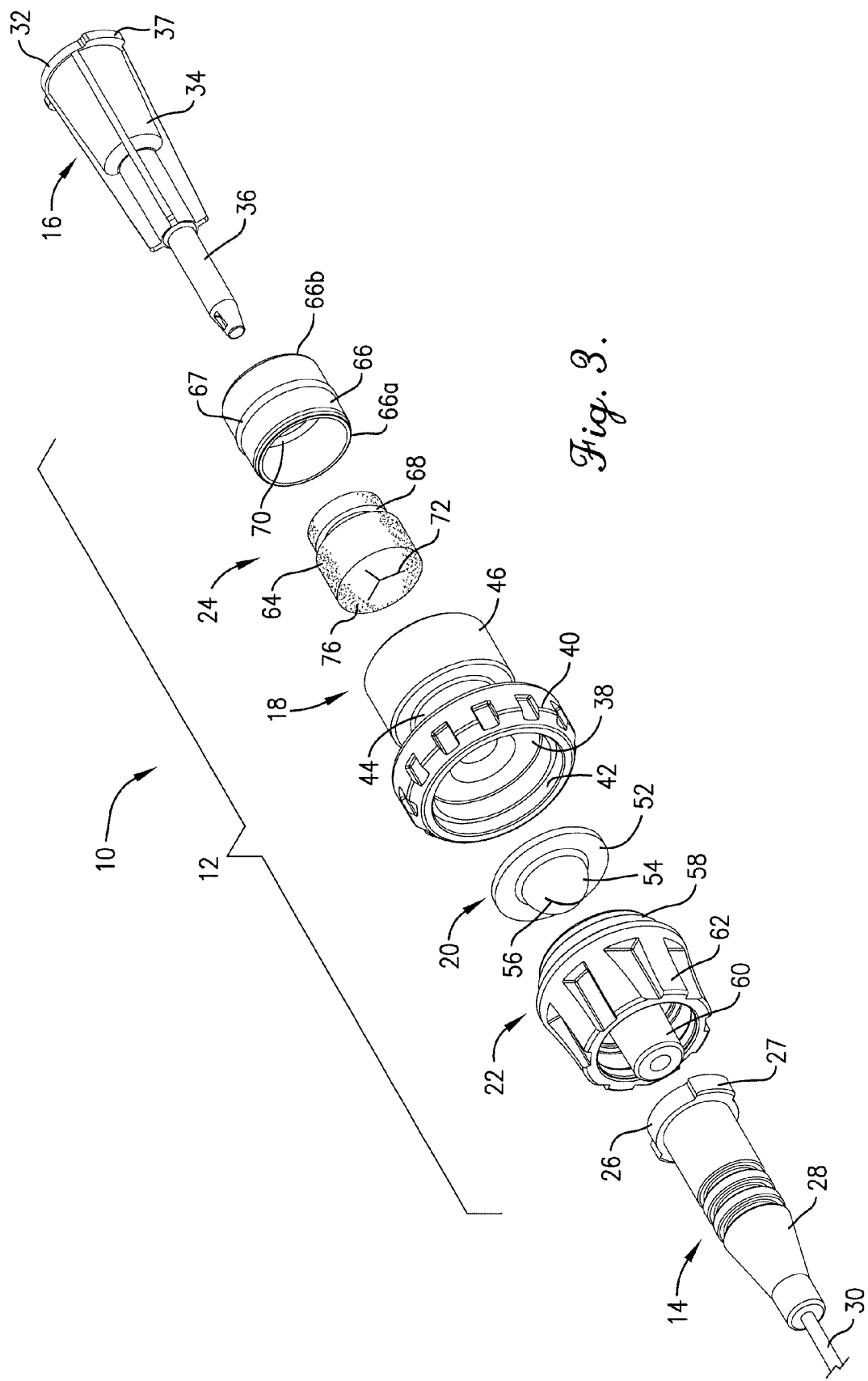
FIG. 3 is an exploded perspective view of the injection site depicted in FIG. 1, illustrating the assembly from the opposite side as compared with FIG. 2.

The drawing figures do not limit the present invention to the specific embodiments disclosed and described herein. The drawings are not necessarily to scale, emphasis instead being placed upon clearly illustrating the principles of the preferred embodiment.

DETAILED DESCRIPTION OF THE PREFERRED EMBODIMENT

Turning now to the drawings, the intravenous catheter assembly 10 selected for illustration generally includes an injection site 12, a peripheral catheter 14 secured to the distal end of the site 12, and a cannula 16 removably inserted into the proximal end of the injection site. The injection site 12 is constructed in accordance with a preferred embodiment of the present invention. Although the injection site 12 is shown with the catheter 14 and cannula 16, it will be appreciated that the site 12 can be used in other applications (e.g., with other types of connection components, tubing, etc.). The injection site 12 preferably includes a support body 18, distal components comprising a unitary pressure-actuated flow control valve 20 and luer lock fitting 22, and a proximal split septum unit 24. As will be apparent with respect to certain aspects of the present invention, the injection site 12 may itself be alternatively configured (e.g., a luer lock fitting may not be required).

In more detail, the illustrated peripheral catheter 14 is itself entirely conventional, having an annular proximal base 26 with diametrically opposed connection tabs 27 for threaded connection to the fitting 22. The catheter 14 also includes a distally extending barrel 28 and cannula 30 secured to the distal end of the barrel 28. As is customary, the cannula is inserted into a patient so that medicaments can be injected and fluids can be aspirated via the injection site 12. As previously mentioned, the principles of the present invention are equally applicable to other catheter designs, as well as other components permanently or removably secured to the injection site 12.

The illustrated cannula 16 is also conventional in construction and preferably includes a proximal annular base 32 and an externally ribbed barrel 34 terminating in an elongated injection lumen 36. The base 32 is preferably provided with diametrically opposed connection tabs 37 configured for threaded connection with a standard luer lock fitting. It is particularly noted that the cannula 16 is a so-called "blunt cannula," preferably formed of a relatively rigid plastic and intended to provide needleless connection with a septum. Although a needle could conceivably be used with the injection site 12, those ordinarily skilled in the art will appreciate that a split septum is typically designed for use with a blunt cannula.

The support body 18 is preferably a molded synthetic resin rigid body having a cup-like structure presenting an annular valve seat 38 as well as a distally extending sidewall 40. The sidewall 40 is provided with a stepped inner connection surface 42. Additionally, the support body 18 has a proximally extending, tubular mid-section 44 which supports a radially expanded, annular septum well 46. The well 46 has an inner annular connection groove 48. As best seen in FIGS. 4 and 5, the well 46 also has an inner septum-engaging surface 50 which defines a central passageway 51.

As will be explained in more detail, the surface 50 is designed to restrict distal displacement of the septum when the cannula 16 is inserted therein and, more preferably, precompress the septum prior to cannula insertion. As perhaps best shown in FIGS. 4 and 5, the surface 50 projects proximally to provide the desired degree of precompression. Specifically, the surface 50 is rounded with a central apex through which the passageway 51 extends. The surface preferably extends in a proximal direction at least about 0.015, of an inch (measured axially from the distalmost circumferential periphery to the central apex). More preferably, the "height" of the surface is about 0.026, of an inch.

The passageway 51 is preferably configured and dimensioned to ensure the surface 50 provides the desired contact with and preloading of the septum, while the cannula 16 is inserted and removed. That is to say, it is most desirable to provide the greatest degree of contact between the surface 50 and split septum. Because the illustrated cannula 16 extends past the surface 50, the passageway 51 preferably has a diameter that complements the outer diameter of the lumen 36. It has been determined that the most preferred radial clearance between the surface 50 and lumen 36 is about 0.006, of an inch, which provides the desired contact while avoiding interference with flow through the lumen 36. Furthermore, the diameter of the passageway 51 is preferably no more than about thirty-five percent (35%) greater than the outer diameter of the lumen 36. With regard to known catheter dimensions, the preferred passageway 51 has a diameter in the range of about 0.099, of an inch to about 0.112, of an inch. In the illustrated embodiment, the passageway 51 is dimensioned to accommodate all known cannula sizes and has a diameter of about 0.112, of an inch.

The valve 20 has a peripheral flange 52 as well as a concavo-convex, substantially dome-shaped central body 54. The body 54 is of progressively decreasing thickness leading to its apex, and has a normally closed slit 56 formed therein. The entire valve 20 is integrally formed from resilient synthetic resin and is of the type describe in detail in US Patent Application Publication 2005/0010176,, incorporated by reference herein. As illustrated, the flange 52 is configured to rest upon seat 38 with the body 54 extending distally. As will be discussed, the valve 20 is preferably designed to selectively prevent fluid flow in the proximal direction (corresponding to aspiration through the injection site 12). More particularly, the valve 20 prevents proximal flow when the pressure differential across the valve is below a certain amount. This amount corresponds to the normal pressure differential experienced by the valve when fluid is not being purposefully infused or aspirated through the injection site 12. That is to say, when the valve experiences the typical venous pressure of the patient, the pressure differential is not sufficient to open the valve. However, when it is desired to infuse or aspirate fluid across the valve, the pressure differential is sufficient to open the valve and fluid passes through the slit 56. It is also noted that the valve 20 is preferably configured so that the pressure differential required to open the valve is greater when aspirating as opposed to infusing.

The luer lock fitting 22 is formed of rigid synthetic resin and is generally of conventional design. However, the fitting 22 includes a proximal connection end 58 designed to mate with connection surface 42 of valve-supporting sidewall 40, thereby sandwiching the valve periphery 52 between the seat 38 and the annular, proximal butt end of the fitting 22. As is customary, the fitting 22 includes a distally extending annular inner barrel 60 and outer, annular, internally threaded connection wall 62. As best seen in FIGS. 4 and 5, the annular base 26 of peripheral catheter 14 is threaded into the fitting 22, between the inner barrel 60 and outer connection wall 62.

The split septum unit 24 is preferably made up of two components, namely a resilient elastomeric (e.g., polyisoprene) septum body 64, and an annular rigid synthetic resin septum holder 66. It will be noted, however, that certain aspects of the present invention do not require the holder 66. The illustrated holder 66 has opposed, annular, distal and proximal ends 66a, 66b, and is disposed about body 64. The outer surface of the holder 66 also has an outwardly projecting, annular detent 67. As illustrated, the outer periphery of resilient body 64 has an annular groove 68, while the inner surface of holder 66 is equipped with a mating, annular rib 70; the interfit of rib 70 into groove 68 securely fastens the holder 66 to body 64. The internal diameter of the ring-shaped septum holder 66 and the outer diameter of the septum body 64 are preferably dimensioned to closely complement one another, whereby the septum holder 66 provides little or no preloading of the septum body 64.

The body 64 also has a split 72 extending fore and aft between the proximal and distal faces 74, 76 thereof. This allows insertion of cannula 16 through the septum unit 24, as will be described. The split 72 is preferably a tri-slit (or Y-shaped slit), although a linear split or other split configurations are entirely within the ambit of the present invention. The body 64 and holder 66 are configured similar to that disclosed and claimed in the Wyatt patents, which are hereby incorporated by reference herein. However, those ordinarily skilled in the art will appreciate that ceratin principles of the present invention are not limited to the illustrated septum design (e.g., the septum holder 66 is not always required, the design of the septum body 64 may be varied, such as changing the configuration of the split, etc.).

In the illustrated embodiment, the holder 66 projects proximally outward from the well 46 so that the proximal terminal face 74 of the holder 66 is spaced outwardly from the proximal terminal edge of the support body 18. Moreover, the body 64 and holder 66 are preferably configured to present a substantially coplanar proximal septum surface (cooperatively defined by faces 66b, and 74). This arrangement provides a generally smooth swabable surface that greatly enhances the cleanliness of the site 12. It is entirely within the ambit of certain aspects of the present invention to provide the site 12 with an alternative proximal configuration. For example, the proximal surfaces of septum body, septum holder, and well may alternatively be axially offset relative to one another. Furthermore, if desired, the proximal face of the well 46 could also be coplanar with the faces 66b, and 74. In the preferred embodiment, the faces 66b and 74 are not coplanar until the unit 24 is received within the well 48, whereupon the septum body 64 is preloaded and deflected proximally into flush relationship with the proximal face 66b.

The septum unit 24 is received within well 46, with the septum body 64 preferably being preloaded as previously described. Furthermore, the unit 24 is inserted into well 48 until the detent 67 is seated within groove 48, which provides further precompression (or at least resistance to radially deflection) of the septum body 64. Yet further, as the septum unit 24 is seated within the well 48, the outer periphery of distal face 76 of body 64 comes into firm contact with the protruding annular well surface 50. Consequently, the body 64 is compressed and assumes a shape complemental with the surface 50 (see FIG. 4).

It is particularly noted that the illustrated septum unit 24 is snap (or compression fit) within the well 48 of support body 18, with the swabable proximal face of the unit (cooperatively formed by faces 66b, and 74) being devoid of connection structure that might prevent or interfere proper cleaning of the swabable face. In other words, the preferred embodiment provides an injection site that eliminates the traditional untoward connection between the septum body and the structure supporting it. In conventional split septum injection sites (not shown), such untoward connection has included a melted plastic ridge formed by the proximal end of the support structure for the septum. In this arrangement, the proximal end of the support structure is heated after the septum is received therein, such that a hard plastic circumferential ridge partially overlaps and extends about the proximal face of the septum body. Those ordinarily skilled in the art will appreciate that the ridge/septum body interface is prone to pathogen contamination.

The design of septum unit 24 affords a number of other significant advantages. First of all, by virtue of the described seating of the unit 24 within well 46, a double seal is effected. That is, a first seal is provided between the periphery of the resilient body 64 and well surface 50, as well as a second hard-surface seal between the interengaged holder 66 and the well walls. This arrangement significantly reduces the risk of undesirable fluid flow between the support body 18 and septum unit 24. Additionally (see FIG. 4), the preloading of body 64 serves to ensure the flush condition between the proximal face 74 of body 64 and the proximal face 66b of the holder 66. Again, this design eliminates surface irregularities or undercut regions which can become contaminated during use.

Very important operational advantages are provided through use of the preloaded septum unit 24. That is, when the intravenous catheter assembly 10 is assembled and catheter 30 is inserted into a patient, the septum unit 24 is at the free end of the assembly 10. Thereupon, a catheter 14 is inserted through slit 72 of body 64 in order to provide a pathway for fluid infusion (e.g., administration of parenteral fluids to the patient) or fluid aspiration (e.g., blood draws). Referring specifically to FIGS. 4 and 5, it will be seen that, as the cannula 16 is inserted into and through septum body 64, the body protrudes proximally as shown at reference numeral 78 in FIG. 5, without any significant distal displacement. This occurs because of the contact between the body 64 and surface 50 and the preloading of the body 64 within well 46. Once the cannula 16 is properly installed, the assembly 10 may then be used in the conventional and well-known fashion.

When cannula 16 is withdrawn for replacement or because a different cannula is to be employed, there is essentially no distal friction-induced displacement of the cannula body 64 as is common in prior art split septum designs. Therefore, there is essentially no creation of negative pressures or septum "drumming" within the assembly 10 which could lead to reflux of blood into the assembly.

The prevention of blood reflux in the assembly 10 is augmented by virtue of the use of the concavo-convex valve 20 in combination with the specialized split septum unit 24. It has been found that this combination essentially completely prevents any blood reflux and is thus especially preferred.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

We claim:

1. An intravenous injection site for connection to a cannula, said injection site comprising:
    a split septum unit including a resilient septum body, wherein the body presents opposite proximal and distal faces and a slit extending therebetween to receive the cannula, said septum body including—
        a terminal proximal face,
        an annular exterior surface,
        a terminal distal face, and
        an annular groove;
    a pressure-actuated flow control valve spaced distally from the septum body and being operable to selectively prevent fluid flow in a proximal direction; and
    a septum support assembly operable to precompress the septum body so that, upon insertion of the cannula, the septum body is displaced proximally to a greater degree than the septum body is displaced distally, said septum support assembly including—
        a terminal proximal face defining a generally horizontal plane,
        an annular internal septum-engaging surface,
        a terminal distal surface that presents a flow-through passageway, and
        an annular inwardly projecting rib,
    wherein at least a portion of said terminal distal surface of the septum support assembly projects proximally relative to the septum body to contact said terminal distal face of the septum body, and further wherein said annular inwardly projecting rib of the septum support assembly is interfit with said groove of the septum body, such that the septum body is precompressed between the terminal distal surface and the rib of the septum support assembly prior to the cannula being inserted in the septum body to substantially restrict distal displacement of the septum body when the cannula is inserted therein,
    wherein there are no spaces or recesses between the annular internal septum-engaging surface of the septum support assembly and the annular exterior surface of the septum body, and further wherein there are no spaces or recesses between the terminal distal surface of the septum support assembly and the terminal distal face of the septum body,
    wherein said proximal displacement of said septum body upon insertion of the cannula extends proximally beyond said horizontal plane defined by said terminal proximal face of the septum support assembly, and
    wherein at rest, said terminal proximal face of the septum body is substantially coplanar with the terminal proximal face of the septum support assembly.

2. The intravenous injection site as claimed in claim 1, wherein said portion of said septum-engaging surface that projects proximally has a convex shape,
    said septum-engaging surface serving to precompress the septum body prior to the cannula being inserted therein.

3. The intravenous injection site as claimed in claim 2, said flow-through passageway being centrally located and presenting a diameter between about 0.099 of an inch and about 0.112 of an inch.

4. The intravenous injection site as claimed in claim 2,
    said septum-engaging surface presenting an outer periphery and a proximally spaced central apex,
    said periphery and said apex being spaced apart approximately 0.026 of an inch.

5. The intravenous injection site as claimed in claim 4, said flow-through passageway being located at the apex and presenting a diameter between about 0.099 of an inch and about 0.112 of an inch.

6. The intravenous injection site a claimed in claim 2,
    said septum unit including a septum holder disposed about the septum body,
    said septum holder forming at least in part the septum support assembly.

7. The intravenous injection site as claimed in claim 6; and
    a support body supporting the septum unit and thereby forming in part the septum support assembly,
    said support body including a well in which the septum unit is received, with connection structure being provided between the well and the septum holder to precompress the septum body prior to the cannula being inserted in the septum body.

8. The intravenous injection site as claimed in claim 7,
    said connection structure comprising a groove formed in one of the well and the septum holder and a detent formed in the other of the well and the septum holder, with the groove receiving the detent.

9. The intravenous injection site as claimed in claim 1,
    said valve preventing fluid flow in the proximal direction when fluid pressure differential across the valve is below a predetermined amount 10. The intravenous injection site as claimed in claim 9;
    a support body supporting the septum unit and thereby forming at least in part the septum support assembly; and
    a luer lock fitting fixed to the support body,
    said valve being captured between the support body and the luer lock fitting.

11. The intravenous injection site as claimed in claim 1,
    said split septum unit including a septum holder disposed about the septum body; and
    a support body supporting the split septum unit and including a septum well receiving the septum unit therein, with a first seal being defined between the bodies and a second seal being defined between the septum holder and the support body,
    said septum holder and said support body each forming in part the septum support assembly.

12. The intravenous injection site as claimed in claim 1,
    said proximal face of the septum support assembly being devoid of connection structure for connecting or holding said septum body within said septum support assembly,
    said proximal faces of the septum support assembly and the septum body being substantially flush to cooperatively present a substantially smooth swabable proximal surface.

* * * * *